(12) United States Patent
Dohm et al.

(10) Patent No.: US 9,040,792 B2
(45) Date of Patent: *May 26, 2015

(54) OSTEOSPERMUM AND DIMORPHOTECA PLANTS HAVING AN ALTERED FLOWER PHENOTYPE

(75) Inventors: Andrea Dohm, Pforzheim (DE); Ulrich Sander, Stuttgart (DE); Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 189 days.

This patent is subject to a terminal disclaimer.

(21) Appl. No.: 12/750,965

(22) Filed: Mar. 31, 2010

(65) Prior Publication Data

US 2011/0247092 A1    Oct. 6, 2011

(51) Int. Cl.
    *A01H 5/02*    (2006.01)

(52) U.S. Cl.
    CPC ..................................... *A01H 5/025* (2013.01)

(58) Field of Classification Search
    None
    See application file for complete search history.

(56) References Cited

U.S. PATENT DOCUMENTS

| | | | |
|---|---|---|---|
| 5,684,225 | A | 11/1997 | Drewlow et al. |
| PP10,342 | P * | 4/1998 | Sorensen ................ Plt./360 |
| 6,150,591 | A | 11/2000 | Hanes et al. |
| PP12,020 | P2 | 7/2001 | Rother |
| PP12,149 | P2 | 10/2001 | Rother |
| PP15,816 | P2 * | 6/2005 | Kawashima ............ Plt./360 |
| PP15,866 | P2 * | 7/2005 | Kawashima ............ Plt./360 |
| PP16,564 | P3 | 5/2006 | Larsen |
| PP17,419 | P2 | 2/2007 | Larsen |
| PP17,703 | P3 * | 5/2007 | Larsen ..................... Plt./360 |
| PP18,330 | P3 | 12/2007 | Kaagman |
| PP23,304 | P2 | 1/2013 | Klemm et al. |
| PP23,388 | P3 | 2/2013 | Klemm et al. |
| 8,759,646 | B2 | 6/2014 | Dohm et al. |
| 2011/0247105 | A1 | 10/2011 | Dohm et al. |

FOREIGN PATENT DOCUMENTS

| | | |
|---|---|---|
| EP | 10158786.3 | 8/2010 |
| EP | 11160693.5 | 10/2011 |
| EP | 11160693.5 A1 | 10/2011 |
| EP | 13187479.4 A1 | 1/2014 |

OTHER PUBLICATIONS

Giovannini et al ISHS ACTA Horticulturae 508: XIC International Symposium on Improvement of Ornamental Plants, 508:129-133 (2000).*
DeJong, J., et al., "Genetic Analysis in *Chrysanthemum morifolium*. II. Flower Doubleness and Ray Floret Corolla Splitting," Euphytica 33: 465-470 (1984).
Drennan, D., et al., "Heritability of Inflorescence and Floret Traits in *Gerbera*," Euphytica 35: 319-330 (1986).
Börstling, D., "Transformation von Zierpflanzen: Methoden und Anwendungen," Technische Universität München, Jun. 13, 2001.
Allavena, A., et al., "Genetic Engineering of *Osteospermum* SPP: A Case Story," ISHS ACTA Horticulturae 508: XIX International Symposium on Improvement of Ornamental Plants, 508: 129-133 (2000).
Al-Atabee, J. S., et al., "Plant Regeneration from Protoplasts of *Dimorphotheca* and *Rudbeckia*," Plant Cell Reports, 6(6): 414-416 (1987).
Rabaglio, M., et al., "Manipolazione In Vitro Della Dimorfoteca (*Osteospermum* SPP.)," !Italus Hortus, 2(3): 56-59 (Jun. 1995).
U.S. Appl. No. 13/077,351, filed Oct. 6, 2011, Dohm, Andrea.
U.S. Appl. No. 13/506,047, filed Mar. 22, 2012, pending, Klemm et al., Sep. 26, 2013.
U.S. Appl. No. 13/506,065, filed Mar. 22, 2012, pending, Klemm et al., Sep. 26, 2013.
Christie, B.R. and Choo, T.M., Effects of harvest time and Alar-85 on seed yield of red clover, Canadian Journal of Plant Science, vol. 70, No. 3, 1990, pp. 869-871.
Faccioli et al. Plant Breeding, 2000; 119:351-355.
Allavena et al. Acta Hort, 508: 129-133, ISHS 2000.
Berio et al., Acta Hort, 546: 171-176, ISHS 2001.

* cited by examiner

*Primary Examiner* — David H Kruse
(74) *Attorney, Agent, or Firm* — Barbara Campbell; Cochran Freund & Young LLC

(57) ABSTRACT

The present invention relates to an *Osteospermum* and *Dimorphoteca* plant, seed, variety, and hybrid. Another aspect of the present invention relates to an *Osteospermum* and *Dimorphoteca* plant having a mutant allele designated KLEDF which results in an altered flower phenotype. The invention also relates to crossing *Osteospermum* and *Dimorphoteca* plants containing the KLEDF mutant allele with other *Osteospermum* and *Dimorphoteca* plants lacking the KLEDF mutant allele to produce intergeneric and interspecific hybrids. This invention further relates to specific lines of *Osteospermum* varieties exhibiting the altered-flowering phenotype. Furthermore, the invention relates to pollen, seed, and sexual, as well as asexual progeny of such plants with altered flowers. In addition, the invention relates to methods for propagating said plants and to uses of said plants.

32 Claims, 12 Drawing Sheets

OSTEOSPERMUM AND DIMORPHOTECA PLANTS HAVING AN ALTERED FLOWER PHENOTYPE

BACKGROUND OF THE INVENTION

The instant invention relates to an altered flower phenotype in plants belonging to the genera *Osteospermum* and *Dimorphoteca*, which is induced by a mutant allele, as well as to the method of breeding *Osteospermum* and *Dimorphoteca* plants having this altered flower phenotype. All publications cited are hereby incorporated by reference.

The genus *Osteospermum* was introduced as a commercial bedding plant in the beginning of the nineties of the last century. Since then this genus has been very successful in the horticultural market. For 2008, worldwide sales were estimated at almost 100 million plants.

The genus *Osteospermum* is a South African native and belongs to the plant family of the Asteraceae. It comprises almost 70 different species representing a broad range of either evergreen shrubs or herbaceous plants with growing habits varying from erect to prostrate. The existing *Osteospermum* cultivars are thought to be interspecific hybrids of the following main species: *O. ecklonis*, *O. barbariae*, *O. caulescens*, *O fruticosum*, *O. jucundum*, and *O. chrysanthemifolia*. The first breeding with *Osteospermum* was started between 1970 and 1985 by British hobby breeders and later continued mainly by Danish and Japanese breeders (Allavena, A., et al., Genetic engineering of *Osteospermum* ssp.: a case story, *Acta Hort.*, 508, 129-133 (2000)). According to Faccioli, et al., professional breeders used the British plant material as well as accessions from South Africa to breed new hybrids (Faccioli, P., et al., Genetic diversity in cultivated *Osteospermum* as revealed by random amplified polymorphic DNA analysis, *Plant Breed.*, 119, 351-355 (2000)). During further breeding, which was mainly done by professional Danish and German breeding companies, crossings between the existing varieties were made to improve the quality. This approach has resulted in a narrow gene pool of the plant material, which is commercially available today. For commercial production, *Osteospermum* and *Dimorphoteca* plants are mostly propagated asexually by cuttings. However, sexual propagation through seeds is also possible and several seed propagated varieties are on the market.

The genera *Osteospermum* and *Dimorphoteca* are very closely related and, in some cases even the distinction of both genera or the classification of certain varieties into these two genera is unclear. In the past the genus *Osteospermum* belonged to the genus *Dimorphoteca*, but today *Dimorphoteca* only comprises the annual species, whereas all semi-perennial species fall into the genus *Osteospermum*. Cross-breeding between both genera is possible and several commercial varieties result from interspecific hybridisation between an *Osteospermum* and a *Dimorphoteca* parent. The different *Osteospermum* and *Dimorphoteca* cultivars, breeding lines and wild species represent a broad range of different ploidy levels varying from 2× up to almost 8×, which also shows that during the development of today's cultivars hybridisation between species took place.

Commercially available *Osteospermum* plants flower from early spring to autumn. The typical flower is a capitulum (flower head) with tubular central disc florets surrounded by a ring of ray florets, which gives the flowers the typical daisy shape (Faccioli, P., et al., Genetic diversity in cultivated *Osteospermum* as revealed by random amplified polymorphic DNA analysis, *Plant Breed.*, 119: 351-355 (2000)). Colour and shape of ray florets as well as the colour of the disc florets vary. The colour of the upper surface of the ray florets, which in colloquial language are called petals, is determined by two independent metabolic pathways producing carotenoids, visible as yellow-orange-brown colours, and anthocyanins, resulting in white to pink and purple flower colours (Seitz, C., Klonierung and Charakterisierung von Flavonoid-genen aus *Osteospermum*, Dissertation an der Technischen Universität München (2004)). Intensive breeding work during the past several years has resulted in a broad range of white, pink, purple, yellow, and orange petal colours and new mixes of the carotenoid and anthocyanin colour groups, as well as in colour patterns like eye types or stripes. Similar to the colour range of the upper surface, the colour of the lower surface of the ray florets also varies from light to dark colours in the bluish-pink or yellow-brown colour range. The colour pattern usually is striped with the coloured stripes running parallel to the petal edges. Typically, the colour of the disc florets is darker than the colour of the ray florets and it may vary from grey to blue, violet or purple or from dark yellow to dark brown. The usual shape of the ray floret is obovate, but in some genotypes the petal edges are rolled upwards resulting in so-called spoon or spider types.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary, not limiting in scope. In various embodiments, one or more of the above-described problems have been reduced or eliminated, while other embodiments are directed to other improvements.

The invention relates to an altered flower phenotype in *Osteospermum* and *Dimorphoteca* expressed in the formation of enlarged or converted disc florets. This altered flower type is induced by a mutant allele. The invention additionally relates to new *Osteospermum* and *Dimorphoteca* plants characterized by their unique flowers which may be produced by the described methods. Furthermore, the invention relates to pollen, seed, and sexual, as well as asexual progeny of such plants with altered flowers. In addition, the invention relates to methods for propagating said plants and to uses of said plants. Finally, the invention relates to a method for breeding *Osteospermum* and *Dimorphoteca* plants having the mutant allele of the invention also by using interspecific hybridisation between both genera and resulting in hybrids having the altered flower shape.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Altered flower. As used herein "altered," "converted," and "enlarged" flower, flowers, flowering, floret, and florets are used interchangeably and refer to *Osteospermum* or *Dimor-*

*photeca* plants producing inflorescences with significantly enlarged disc florets. These enlarged disc florets are on average longer than 0.8 cm, whereas the length of disc florets in normal or typical flowering plants is on average less than 0.8 cm. The enlarged disc florets may still be tubular and enclose the gynoecium and androecium (FIG. 2 and FIG. 5) or the enlarged disc florets may be further extended and open and they may be transformed into ligulate florets (FIG. 3 and FIG. 6) resulting in a double flowering phenotype. All transitions of these two phenotypes may occur in plants of the present invention.

Androecium. Male parts of a plant flower (collectively termed the stamens).

Asexual propagation/Asexual reproduction. Asexual propagation or reproduction means every type of plant propagation apart from seeds, e.g., by cuttings, grafting, division, or regeneration in tissue culture.

Backcrossing. Backcrossing is a process in which a breeder repeatedly crosses hybrid progeny back to one of the parents, for example, a first generation hybrid $F_1$ with one of the parental genotypes of the $F_1$ hybrid.

Capitulum. Capitulum refers to an inflorescence in the form of a central disc of sessile flowers called disc florets and an outer ring of petal-like structures called ray florets. The disc florets are generally perfect while the ray florets are generally imperfect.

Cell. Cell as used herein includes a plant cell, whether isolated, in tissue culture, or incorporated in a plant or plant part.

Chimera. A chimera or a chimeric plant is a plant that consists of two or more genetically distinct groups of cells. The genetic distinctness usually originates from a mutation.

Disc floret. One of the small tubular, actinomorphic florets which make up the central part of the flower head in Compositae or Asteraceae plants.

Dominant inheritance. Refers to a mode of inheritance in which the phenotype of a certain characteristic or trait is determined by a dominant allele.

Dominant mutation. The phenotype of a dominant mutation is visible in a heterozygous genotype.

Double flower. In the Asteraceae or Compositae plant family, the term "Double flower" or "Semi-double flower" refers to inflorescences which have more than one whorl of ray florets. In completely "double-flowering" plants, all disc florets are transferred into ray florets, whereas in "semi-double-flowering" plants, only several whorls of disc florets are mutated into ray florets.

Embryo. The embryo is the small juvenile plant contained within a mature seed.

$F_2$. The "$F_2$" symbol denotes a generation resulting from the selfing of the $F_1$ generation along with selection for type and rogueing of off-types. The "F" number is a term commonly used in genetics, and designates the number of the filial generation. The "$F_2$" generation denotes the offspring resulting from the selfing or self mating of members of the generation having the next lower "F" number, viz. the $F_1$ generation.

Gene. As used herein, "gene" refers to a segment of nucleic acid. A gene can be introduced into a genome of a species, whether from a different species or from the same species, using transformation or various breeding methods.

Gene-environment interaction/Genotype-environment interaction. Refers to the phenotypic effect of interactions between genes and the environment.

Genetic transformation. Refers to the genetic alteration of a cell resulting from the uptake, genomic incorporation, and expression of foreign genetic material.

Gene converted (Conversion). Gene converted (conversion) plants refers to plants which are developed by a plant breeding technique called backcrossing wherein essentially all of the desired morphological and physiological characteristics of a variety are recovered in addition to the one or more genes transferred into the variety via the backcrossing technique, genetic engineering or mutation.

Genotype. Refers to the genetic constitution of a cell or organism.

Gynoecium. The ovule producing parts of a plant's flower.

Heterozygous. Refers to a genetic constitution in which the corresponding alleles of a certain gene locus are different.

Homozygous. Refers to a genetic constitution in which the corresponding alleles of a certain gene locus are identical.

Inbreeding depression. Inbreeding depression is the reduced fitness in a given population as a result of breeding of close relatives or in plants also resulting from self pollination.

Inflorescence. A group or cluster of flowers arranged on a stem that is composed of a main branch or an arrangement of branches.

Intergeneric cross. Intergeneric cross means the sexual hybridization of two individuals, each from a different genus.

Intergeneric hybrid. Intergeneric hybrid means a plant of the $F_1$ generation resulting from an intergeneric cross or a cross between two different genera.

Interspecific cross. Interspecific cross means the sexual hybridization of two individuals, each from different species.

Interspecific hybrid. Interspecific hybrid means a plant of the $F_1$ generation resulting from an interspecific cross or a cross between two different species.

Locus. A locus confers one or more traits such as, for example, herbicide tolerance, insect resistance, disease resistance, flower colour, flower shape, plant height, etc. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

M0. The M0 generation is the generation treated with a mutagen.

Monogenic inheritance. Refers to a mode of inheritance in which the phenotype of a certain characteristic or trait is determined by a single gene.

Mutation. Mutations are changes in the DNA sequence of a cell's genome and are caused by mutagens like radiation or chemicals as well as by errors that occur during DNA replication.

Normal flower. As used herein "normal," "typical," "usual," and "regular" flower, flowers, flowering, floret, and florets are used interchangeably and refer to currently available commercial *Osteospermum* and *Dimorphoteca* plants which produce inflorescences with tubular disc florets enclosing but standing below the mature gynoecium and androecium, the disc florets having an average length of less than 0.8 cm (see FIG. 1 and FIG. 4).

Phenotype. Refers to any observable characteristic or trait of an organism like flower colour, plant size, etc.

Plant. As used herein, the term "plant" includes reference to an immature or mature whole plant, including a plant from which seed or anthers have been removed. Seed or embryo that will produce the plant is also considered to be the plant.

Plant Parts. As used herein, the term "plant parts" (or an *Osteospermum* or *Dimorphoteca* plant, or a part thereof) includes, but is not limited to, protoplasts, leaves, stems, roots, root tips, anthers, pistils, seed, embryo, pollen, ovules, cotyledon, hypocotyl, capitulum, ray petal/floret, disc petal/floret, shoot, tissue, petiole, cells, meristematic cells, and the like.

Pollination. Pollination is the process by which pollen is transferred in plants, thereby enabling fertilization and sexual reproduction.

Progeny. As used herein, includes an $F_1$ *Osteospermum* or *Dimorphoteca* plant produced from the cross of two *Osteospermum* or *Dimorphoteca* plants and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Protoplast fusion/Somatic fusion. Refers to a breeding method in plants by which protoplasts (i.e., plant cells without cell walls) from two different plants are fused together to form a new hybrid plant with the characteristics of both.

Quantitative Trait Loci (QTL). Quantitative trait loci (QTL) refer to genetic loci that control to some degree numerically representable traits that are usually continuously distributed.

Ray floret. A ray floret or ligulate floret, is one of the outer, irregular florets in the flower heads of some Compositae or Asteraceae plants. Colloquial in Asteraceae or Compositae plants the ray florets are called petals.

Recessive inheritance. Refers to a mode of inheritance in which the phenotype of a certain characteristic or trait is determined by a recessive allele.

Recessive mutation. The phenotype of a recessive mutation is visible only in a homozygous genotype.

Regeneration. Regeneration refers to the development of a plant from tissue culture.

Sexual propagation/Sexual reproduction. Refers to the propagation of plants from seeds.

BRIEF DESCRIPTION OF THE FIGURES

Exemplary embodiments are illustrated in referenced Figures. It is intended that the embodiments and Figures disclosed herein are to be considered illustrative rather than limiting.

DETAILED DESCRIPTION OF THE INVENTION

Figure 1:
FIG. 1 shows a close-up of a normal flowering *Osteospermum*.
Figure 2:
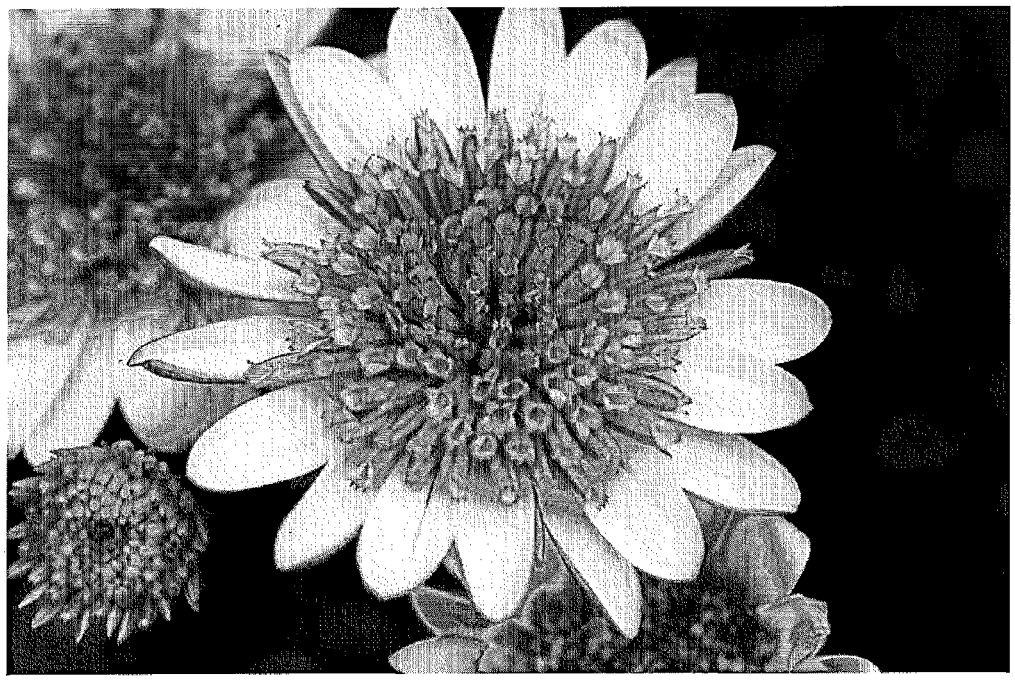
FIG. 2 shows a close-up of an altered flowering *Osteospermum* with enlarged tubular disc florets enclosing the gynoecium and androecium.
Figure 3:
FIG. 3 shows a close-up of an altered flowering *Osteospermum* with enlarged open disc florets partly transformed into ligulate florets.
Figure 4:
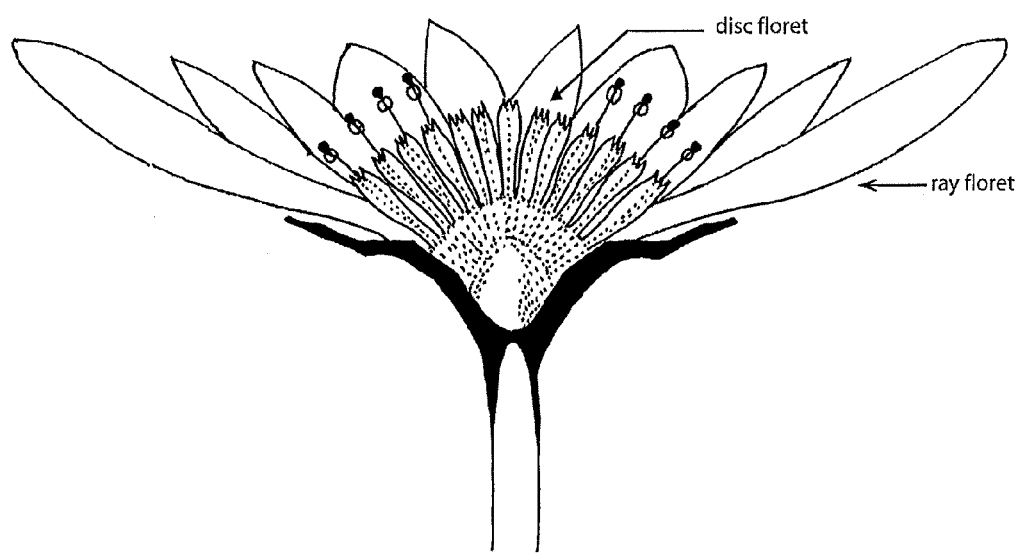
FIG. 4 shows a longitudinal cross-section of a normal flowering *Osteospermum* flower.
Figure 5:
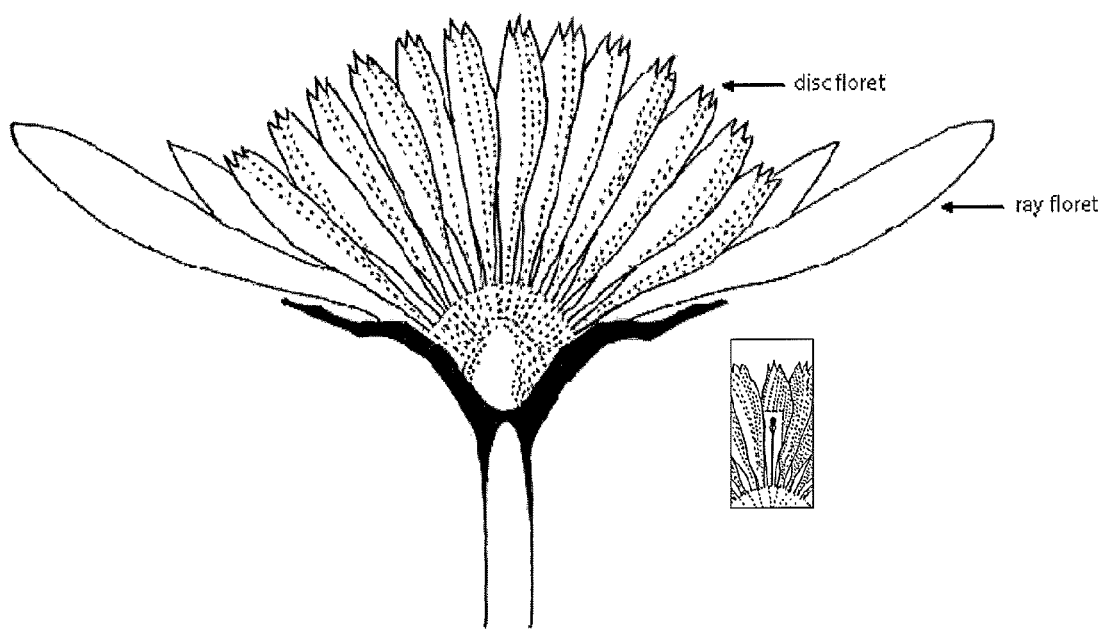
FIG. 5 shows a longitudinal cross-section of an altered flower *Osteospermum* with tubular disc florets.
Figure 6:
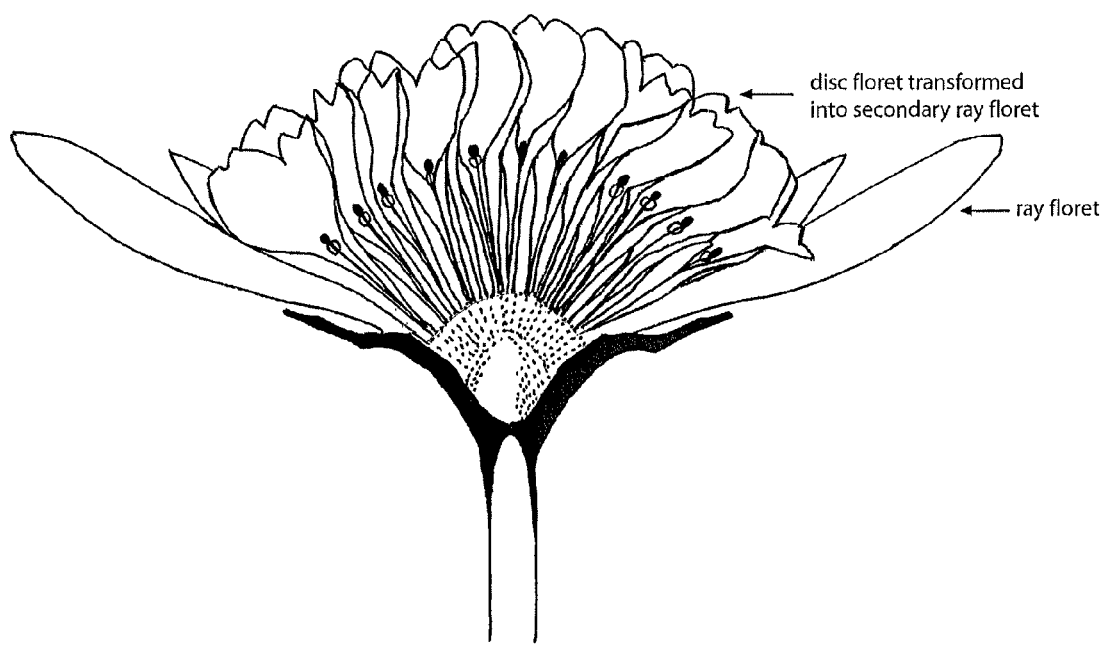
FIG. 6 shows a longitudinal cross-section of an altered flower *Osteospermum* flower with open disc florets.

The altered-flowering plants of the present invention preferably have substantially all altered flowers resulting in a double-flowering phenotype. However, under certain circumstances, only part of the disc florets may be enlarged or only some of the inflorescences are altered inflorescences. This means that the number of enlarged disc florets per inflorescence may vary from only few to more than 100 per inflorescence. All previously known *Osteospermum* and *Dimorphoteca* plants do not have the altered flowers of the present invention. Unexpectedly, the mutant allele of the present invention results in inflorescences having disc florets which are significantly enlarged over the disc florets of previously known *Osteospermum* and *Dimorphoteca* inflorescences.

The new altered-flowering phenotype of the present invention resulting from a mutant allele does not necessarily eliminate the fertility of the flower. The anthers, which are located in the disc floret may be fertile and produce pollen. However, since the anthers are covered by the enlarged disc florets, the pollen is not visible and not freely available for insects. Therefore, in the field plants with the altered-flowering phenotype show significantly reduced seed set originating from insect pollination. Seed set usually originates from the gynoecium located at the base of the ray florets, whereas the disc floret gynoecium seems to be degenerated in both typical-flowering varieties and the new altered-flowering plants.

The present invention encompasses *Osteospermum* plants exhibiting an altered flower phenotype and having at least one disc floret with an average length of about 0.8 cm, 0.9 cm, 0.96 cm, 1.01 cm, 1.15 cm, 1.21 cm, 1.26 cm, 1.29 cm, 1.31 cm, 1.34 cm, 1.38 cm, 1.40 cm, 1.42 cm, 1.45 cm, 1.49 cm, 1.51 cm, 1.52 cm, 1.55 cm, 1.57 cm, 1.61 cm, 1.63 cm, 1.64 cm, 1.66 cm, 1.69 cm, 2.0 cm, 2.01 cm, 2.1 cm, 2.16 cm, 2.19 cm, 2.23 cm, 2.26 cm, 2.28 cm, 2.30 cm, 2.33 cm, 2.36 cm, 2.37 cm, 2.39 cm, 2.4 cm, 2.45 cm, 2.47 cm, 2.51 cm, 2.56 cm, 2.57 cm, 2.59 cm, 3.60 cm, 3.63 cm, 3.67 cm, 3.71 cm, 3.74, cm, 3.81 cm, 3.82 cm, 3.85 cm, 3.88 cm, 3.89 cm, 3.93 cm, 3.94 cm, 3.96 cm, 4.01 cm, 4.07 cm, 4.09 cm, 4.11 cm, 4.15 cm, 4.17 cm, 4.22 cm, 4.25 cm, 4.29 cm, 4.30 cm, 4.32 cm, 4.33 cm, 4.34 cm, 4.35 cm, 4.38 cm, 4.39 cm, 4.41 cm, 4.42 cm, 4.46 cm, 4.48 cm, 4.50 cm, 4.52 cm, 4.53 cm, 4.55 cm, 4.59 cm, 4.61 cm, 4.63 cm, 4.66 cm, 4.67 cm, 4.68 cm, 4.71 cm, 4.72 cm, 4.81 cm, 4.82 cm, 4.83 cm, 4.88 cm, 4.90 cm, 4.91 cm, 4.93 cm, 4.96 cm, 4.99 cm, 5.01 cm, 5.05 cm, 5.07 cm, 5.11 cm, 5.14 cm, 5.16 cm, 5.18 cm, 5.22 cm, 5.26 cm, 5.34 cm, 5.37 cm, 5.39 cm, 5.42 cm, 5.46 cm, 5.47 cm, 5.50 cm, 5.51 cm, 5.53 cm, 5.58 cm, 5.61 cm, 5.63 cm, 5.67 cm, 5.69 cm, 5.71 cm, 5.72 cm, 5.75 cm, 5.79 cm, 5.80 cm, 5.83 cm, 5.86 cm, 5.87 cm, 5.89 cm, 5.91 cm, 5.93 cm, 5.94 cm, 5.97 cm and 6.0 cm, including all integers and fractions thereof.

The new altered-flowering *Osteospermum* plants are genetically stable, as evidenced by the stability of the altered-type phenotype through asexual propagation and the transmission of this trait to the progeny after sexual crosses.

Attempts to Produce Altered-Flowering *Osteospermum* and *Dimorphoteca*

An *Osteospermum* and *Dimorphoteca* breeding program was established in 2002 to produce altered-flowering *Osteospermum* and *Dimorphoteca* plants. *Osteospermum* plants with unusual inflorescences are desirable in the horticultural market. *Osteospermum* inflorescences with double flowers would be desirable in the horticultural market. Several approaches were attempted to achieve an altered-flowering trait in the genera *Osteospermum* and *Dimorphoteca*. In addition to treatments to induce mutations, experiments on interspecific and intergeneric crosses were also attempted.

Mutation Treatment

Several experiments on induction of mutations by Gamma-irradiation of *Osteospermum* and *Dimorphoteca* plant material were performed. Examples of references that illustrate alteration of flower type via mutation are altered flower type in ornamental sweetpotato, Bhate, R. H., "Chemically induced floral morphological mutations in two cultivars of *Ipomoea purpurea* (L.) Roth," *Scientia Horticulturae.* 88: 133-145 (2001); in *Chrysanthemum*, Rana, R. S., "Radiation-induced variation in ray-floret characteristics of annual *Chrysanthemum*," *Euphytica.* 8: 270-322 (1965); in roses, Teruo, N., Ikegami, Y., Matsuda, Y., and Toyoda, H., "Induction of Morphologically Changed Petals from Mutagen-treated Apical Buds of Rose and Plant Regeneration from Varied Petal-derived Calli," *Plant Biotechnology,* 8: 233-236 (2001); and in plants in general, Krasaechai, A. L. D., et al., "Low-energy ion beam modification of horticultural plants for induction of mutation," *Surface and Coatings Technology,* 203: 2525-2530 (2009). In this regard it is important to mention that the ploidy level of almost all *Osteospermum* cultivars is tetraploid, whereas the ploidy level of *Dimorphoteca* cultivars varies from 2× to 6×. This means that in the case of a recessive mutation at least two generations would be necessary for the phenotype of any recessive mutation to become visible. In the case of a dominant mutation the phenotype would become visible in the M0-generation.

A first set of experiments was performed on mature seeds which had been harvested from different *Dimorphoteca* cultivars. Batches of 30 seeds each were treated with doses of Gamma-irradiation varying from 15 to 40 Gy for periods varying from 5 to 30 minutes. Immediately after this treatment the seeds were soaked in a solution of 10% Polyethylene glycol (PEG) for 4 hours, the solution was washed off and the seeds were sown in standard seedling substrate. Germination started after about one week. Three weeks after sowing, when the first pair of leaves had developed, the seedlings were transplanted. Three weeks after transplanting, the seedlings were planted into 11 cm diameter pots and grown according to standard protocols. First flowering started about 10 weeks after potting. The plant populations were continuously evaluated for effects or mutants caused by the Gamma-irradiation.

Overall, the Gamma-irradiation affected the germination rate. According to the dosage and the period of irradiation fewer seeds germinated and more malformed seedlings appeared, which did not develop further. Alterations of the growing habit as well as altered foliage types were difficult to evaluate, because the seeds originated from crossbreeding and, therefore segregation of these characters in the offspring was expected. However, altered flower colours appeared, which resulted from mutation and not from segregation of the parental flower colours. These new colours showed that overall mutations of flower characteristics had successfully been induced by Gamma-irradiation. However, no altered-flower shapes were detected in these plant populations.

A second set of experiments was performed on rooted cuttings from different *Dimorphoteca* cultivars. Cuttings were rooted in standard paper pots within a period of 4 weeks. After successful rooting the cuttings were pinched above the 5th leaf pair and immediately Gamma irradiated. The dosages and irradiation periods corresponded to the previous experiments on seeds. After irradiation the cuttings were planted into 11 cm diameter pots containing a standard growing substrate and cultivated under standard growing conditions. The young plants were pinched back twice over a period of 6 weeks in order to allow mutated cells to develop into shoots. Flowering started about 13 weeks after planting. The plants were continuously evaluated for mutants. Several altered growing habits, foliage shapes, and flower colours were detected. However, altered flower shapes did not appear on any of the irradiated plants.

Interspecific and Intergeneric Crosses

Representatives from different species of the genera *Osteospermum* and *Dimorphoteca* were collected and crossing experiments with commercial *Osteospermum* cultivars were performed. In all combinations one parent was a commercial variety.

Occasionally, in *Osteospermum* seedling progenies individual plants were detected which exhibited an additional whorl of ray florets. These florets, which were located at the base of the main ray florets, were significantly narrower than the main ray florets and orientated vertically to the first whorl. These flowers still produced female organs at the base of the ray florets and were female fertile which was proved by their seed set. This additional whorl of ray florets was not stable and showed significant genotype-environment interaction. The respective plants were self pollinated as well as crossbred to stabilize this phenotype. However, the trait was not detected in any of the progenies and therefore it is obviously not genetically stable. In summary, interspecific or intergeneric seed set was achieved for only two combinations, which was shown by an intermediate phenotype of the offspring. Among this offspring, as well as in further generations produced from these plants, no stable altered flowering plants were detected.

Development of an Altered *Osteospermum* Flower Phenotype

In spring 2007 in a proprietary population of *Osteospermum* plants, a single plant was found which showed a slightly modified flower phenotype. A more detailed analysis of the flowers on this plant showed that on some of the flowers, the disc florets were elongated and covered the androecium and the gynoecium, whereas in the normal flowers on the same plant the androecium as well as the gynoecium were standing above the disc florets.

The phenotype of this plant was identified as a novelty with a certain potential to be useful for the development of a new flower type within the genus *Osteospermum*. Therefore, further analyses on this plant were performed.

Firstly, it had to be shown if this altered phenotype was the result of a genetic mutation or if it was a modification induced by environmental conditions like the extra whorl of ray florets described above. For this purpose, cuttings from this plant were taken repeatedly, rooted, and grown to flowering plants. Among these plant populations, three different groups of individuals were detected. The first group of individuals was comprised of plants which exhibited only normal flowers, whereas the second group of plants exhibited flowers with the altered phenotype. A further third group of plants consisted of plants which exhibited both types of flowers, the normal type as well as the altered type. This result indicated that the altered flower type could be transmitted by asexual propagation, but it further indicated that this plant was a chimera.

Next, it had to be shown that the new flower type could be transmitted through sexual propagation. Therefore a breeding program with this altered-flowering plant was designed. The sexual transmission of the altered phenotype may depend on the genetic background of the respective crossing parent. Therefore these were carefully selected by their phenotypes and also by their genotypes, making use of a genetic distance analysis which had been performed in the framework of a research project by Gawenda and Debener reported in 2009 (Gawenda, I. and Debener, T., Genetic diversity of *Osteospermum* genotypes analysed by AFLP and chloroplast SSR markers, *Europ. J. Hort. Sci.,* 74 (2), 86-94 (2009)). The normal-flowering *Osteospermum* genotypes, which were used as crossing parents, were all proprietary assortment varieties or breeding lines.

A first series of pollinations was performed as the plant exhibiting the modified flower type was used as a male as well as a female parent. The flowers of the female crossing parents were emasculated before mature pollen appeared. On average, 2 days after emasculation, the stigmas at the base of the ray florets extend which indicates that they are ready for pollination. At this stage they were pollinated repeatedly with pollen from the respective male parent. The use of the altered-flowering plant as the male parent needed specific skills of the pollinators, because the pollen had to be collected carefully at the base of the altered disc florets. About 4 weeks after pollination the seeds were ready for harvesting. In total, 32 crossing combinations had been performed, but only 16 of the combinations produced seeds. In total, almost 5,000 seeds were harvested and sown.

In Table 1, column 1 shows the colour of the ray florets of the respective crossing partners exhibiting normal flower types. Columns 2 through 5 show the number of plants producing normal inflorescences for each colour and the total number of plants. Columns 6 through 9 show the number of plants producing altered inflorescences for each colour and the total number of plants with altered inflorescences. Columns 10 through 13 show the total number of plants for each colour as well as the total number of evaluated seedlings per progeny. Finally, column 14 shows the $\chi^2$-square values for each row which correspond to a 1:1 segregation of altered-flower phenotype to normal-flower phenotype. Asterisks indicate that the respective progenies deviate significantly from a 1:1 segregation at $\chi^2=3.84$.

TABLE 1

Segregation of Flower Type and Flower Colour in $F_1$ Progenies

| Petal colour of the normal flowering crossing partner | # of Normal Flowering Plants | | | | # of Altered Flowering Plants | | | | Total # of Plants | | | | $\chi^2$ Values Corresponding to a 1:1 segregation for flower type |
|---|---|---|---|---|---|---|---|---|---|---|---|---|---|
| | White | Pink | Purple | Total | White | Pink | Purple | Total | White | Pink | Purple | Total | |
| White | 174 | 23 | 41 | 238 | 46 | 5 | 44 | 95 | 220 | 28 | 85 | 333 | *61.4 |
| Purple | 3 | 8 | 263 | 274 | 3 | 3 | 68 | 74 | 6 | 11 | 331 | 348 | *114.8 |
| Pink | 3 | 217 | 33 | 253 | 1 | 7 | 6 | 14 | 4 | 224 | 39 | 267 | *213.94 |
| White | 59 | 28 | 35 | 122 | 23 | 7 | 21 | 51 | 82 | 35 | 56 | 173 | *29.14 |
| White-purple bicoloured | 16 | 12 | 0 | 28 | 3 | 12 | 0 | 15 | 19 | 24 | 0 | 43 | *3.94 |
| Purple | 0 | 9 | 61 | 70 | 0 | 2 | 9 | 11 | 0 | 11 | 70 | 81 | *42.98 |
| Pink | 57 | 59 | 24 | 140 | 5 | 15 | 3 | 23 | 62 | 74 | 27 | 163 | *83.98 |
| Pink | 6 | 47 | 41 | 94 | 0 | 8 | 7 | 15 | 6 | 55 | 48 | 109 | *57.26 |
| Ivory | 110 | 0 | 0 | 110 | 23 | 0 | 0 | 23 | 133 | 0 | 0 | 133 | *56.90 |

For sowing the seeds were soaked in a solution of 10% PEG for 4 hours, the solution was washed off, and the seeds were sown in standard seedling substrate. Germination started after about one week. Three weeks after sowing, when the first pair of leaves had developed, the seedlings were transplanted. Three weeks after transplanting the seedlings were planted into 11 cm diameter pots and grown according to standard protocols. First flowering started about 10 weeks after potting.

The seedling populations were evaluated over a period of 4 weeks mainly focusing on the selection of plants exhibiting the altered flower-type. The progeny comprised 2,459 flowering plants in total. In all progenies plants were selected which showed an altered-flowering phenotype, meaning that these plants had at least one elongated disc floret. The number of altered-flowering plants compared to the total number of seedlings varied among the different progenies. Since the first altered-flowering plant, which was used as a breeding parent, was a chimera, meaning it produced altered-flowers as well as normal flowers on one plant, the segregation pattern was unpredictable, although only altered flowers had been used for pollination. Table 1 summarises the number of altered-flowering and normal-flowering-plants for 9 progenies, which comprised enough seedlings for a segregation analysis. Unexpectedly, the frequency of seedlings exhibiting altered-flowers was in all combinations far from that corresponding to a 1:1-segregation, the expected segregation in case of a dominant inheritance, which is shown by the respective $\chi^2$ values (Table 1). Also unexpectedly none of the progenies exhibited exclusively normal-flowering plants, which would be expected in the case of a recessive inheritance. Furthermore, the data in Table 1 show that the altered-flowering trait is not linked to flower colour.

After sexual propagation by crossbreeding into different Osteospermum cultivars and breeding lines, stable altered-flowering seedlings were found among the $F_1$ progeny. The successful transmission of the altered-flower trait into sexual progeny shows that this trait is genetically stable. However, the segregation pattern of the altered-flower trait in different $F_1$ progenies does not explain the mode of inheritance of this mutation.

For further crossbreeding, 35 altered-flowering or semi-altered-flowering individuals belonging to 12 different half-sibling-populations were selected. These genotypes were crossed among each other as well as with further normal-flowering cultivars. Again the breeding parents were selected according to their phenotype, as well as according to their genetic distance based on the analysis of Gawenda and Debener (Gawenda, I. and Debener, T., Genetic diversity of Osteospermum genotypes analysed by AFLP and chloroplast SSR markers, Europ. J. Hort. Sci., 74 (2), 86-94 (2009)). Pollinations, seed harvest, and sowing as well as cultivation of the seedlings was performed as described above for the $F_1$ progenies. In total, 125 different combinations were made. In total, almost 4,000 seeds were harvested, from which 1,983 seedlings were raised for evaluation. Half of the combinations were crosses between altered-flowering genotypes and normal-flowering varieties. Since the altered-flowering seedlings were not chimeric anymore, the segregation pattern of their offspring with normal-flowering genotypes should correspond to a 1:1 segregation in the case of dominant inheritance. However, as shown in Table 2, this segregation pattern was only found in part of those combinations, which had a sufficient number of individuals for evaluation. The second half of the 125 crossing combinations was made between two altered-flowering genotypes. In the case of a monogenic dominant inheritance a 3:1 segregation pattern of altered-flowering plants to normal-flowering plants would be expected for these progenies. As shown in Table 2, this segregation pattern was unexpectedly only found for 1 of 4 analysed progenies. Therefore, the altered-flowering phenotype may most likely be inherited by a dominant mutant allele, but it might also be the result of two or more genes or a recessive allele.

In Table 2, in the top half of the table, column 1 shows the number of plants having the altered-flowering phenotype resulting from crosses between an altered-flowering $F_1$ plant with a normal-flower plant, while column 2 shows the number of plants having the normal-flowering phenotype and column 3 shows the total number of plants resulting from the crosses. Column 4 shows the $\chi^2$ square values corresponding to the expected 1:1 segregation of altered-flowering phenotypes to normal-flowering phenotypes for each row. In the bottom half of Table 2, the crosses were made between two plants having the altered-flowering phenotype. Asterisks indicate that the respective combinations deviate significantly from the expected 3:1 segregation at $\chi^2$=3.84.

This means, that the combinations, for which the $\chi^2$ square values are below 3.84, correspond to the expected 1:1 or 3:1 segregation pattern for a monogenic dominant inheritance. An * is used to mark those combinations for which the $\chi^2$ squares are above 3.84 and which therefore do not correspond to the expected 1:1 or 3:1 segregation pattern.

The altered-flowering trait was crossbred into different genetic backgrounds representing the available range of growing habits and flower colours in *Osteospermum*. The segregation of plant characteristics like flower colour, flower size, earliness, branching, vigour, and foliage quality in the offspring was according to the segregation patterns in normal-flowering offspring. Surprisingly, these plant characteristics seem not to be linked to the altered flowering trait, as is also indicated by the results presented in Table 3. Furthermore, all individuals which were selected from the different progenies and analysed further performed similarly to typical-flowering *Osteospermum* plants in terms of rooting, cutting production, growing habit and disease/pest resistance. All seedling progenies were grown in Stuttgart, Germany.

However, the closer evaluation of the flower performance evidenced on one hand that altered flowers, which display mainly enlarged disc florets, stay open even in complete darkness, whereas normal flowers close already under low light conditions. Furthermore, the evaluation of the altered-flowering plants in the field showed that the individual flowers kept longer compared to normal-flowering plants. This extended flower keepability is resulting from a reduced seed set due to the limited pollen availability on the altered-flowering plants. Both characteristics are highly desirable in the genus *Osteospermum* and therefore illustrate important breeding targets. Hence, the instant invention overcomes two technical problems which are inherent in the currently available cultivars and breeding material.

In Table 3, column 1 shows the code for each line, column 2 shows whether the line has the altered-flowering phenotype (AF) or the normal-flowering phenotype (NF), columns 3 through 6 show the number of ray florets, the length and width in centimeters of the ray florets and the upper surface colours of the ray florets, respectively. For those plants, which are bicoloured or exhibit playing or fading colours, more than one RHS number is listed. Columns 7 and 8 show the number of disc florets and the length in centimeters of the disc florets, columns 9 and 10 show the length and width in centimeters of the immature leaves, columns 11 and 12 show the length and width in centimeters of the mature foliage, column 13 shows the colour of the mature foliage, and column 14 shows the number of basal shoots for each line.

TABLE 2

Segregation of the Altered-Flower-Type in $F_2$ Progenies

Crosses between altered-flowering $F_1$ plants and normal-flowering plants

| # of Altered-flowering plants | # of Normal-flowering plants | Total # of Plants | $\chi^2$ Values corresponding to a 1:1 segregation pattern |
|---|---|---|---|
| 62 | 90 | 152 | *5.16 |
| 52 | 89 | 141 | *9.70 |
| 60 | 86 | 146 | *4.63 |
| 36 | 38 | 74 | 0.05 |
| 21 | 28 | 49 | 1.00 |
| 21 | 35 | 56 | 3.50 |
| 37 | 29 | 66 | 0.97 |
| 32 | 33 | 65 | 0.02 |

Crosses between two altered-flower-type $F_1$ plants

| # of Altered-flowering plants | # of Normal-flowering plants | Total # of Plants | $\chi^2$ Values corresponding to a 3:1 segregation pattern |
|---|---|---|---|
| 24 | 23 | 47 | *17.03 |
| 41 | 18 | 59 | 0.96 |
| 39 | 38 | 77 | *22.34 |
| 11 | 16 | 27 | *16.91 |

TABLE 3

Comparison of Certain Plant Characteristics between Normal- and Altered-Flowering *Osteospermum* Genotypes

| | | Ray florets | | | Disc florets | | Foliage - Immature | | Foliage - Mature | | | No. |
|---|---|---|---|---|---|---|---|---|---|---|---|---|
| Code | Type | No. | Length (cm) | Width (cm) | Colour (RHS) | No. | Length (cm) | Length (cm) | Width (cm) | Length (cm) | Width (cm) | Colour (RHS) | basal shoots |
| OE 2008248 | AF | 14-16 | 3.0 | 0.7 | 92D | 80-85 | 1.3-2.1 | 3.5 | 0.9 | 4.8-5.0 | 1.6-1.9 | 146A | 6 |
| OE 2008258 | AF | 17-18 | 2.6-2.7 | 0.7-0.8 | 92D | 73-89 | 1.0-1.9 | 3.2 | 0.8 | 5.2 | 1.9-2.0 | 144A | 5 |
| OE 2008274 | AF | 25 | 2.6-2.9 | 0.7-0.9 | 78B | 95-96 | 1.3-1.7 | 3.2 | 0.8-0.9 | 4.5-4.9 | 2.0 | 146A | 5 |
| OE 2008285 | AF | 22-25 | 2.6-3.0 | 0.6-0.8 | N74B | 78-85 | 0.8-2.2 | 4.0-4.5 | 1.2-1.6 | 7.0-7.5 | 2.5-3.5 | 137A | 5 |
| OE 2008384 | AF | 23-27 | 2.1 | 0.6-0.7 | 72A | 94-108 | 1.4-1.7 | 3.4 | 1.1 | 4.1 | 2.1 | 146A | 4 |
| OE 2008390 | AF | 19-22 | 2.6 | 0.8-0.9 | 77C + 75D | 68-100 | 1.4-1.8 | 3.3 | 0.9-1.1 | 6.5 | 2.0-2.5 | 146A | 5 |
| A-5-43 | NF | 17-20 | 3.2-3.3 | 1.0 | 155D | 65-90 | 0.5-0.6 | 3.3-3.9 | 1.0-1.2 | 6.0-7.0 | 2.3-2.5 | 146A | 4 |
| V 78 | NF | 19-22 | 3.3-3.4 | 1.1-1.2 | 155D | 81-89 | 0.4-0.6 | 3.5-4.0 | 0.9-1.2 | 6.2-7.3 | 2.1-2.4 | N137B | 5 |
| W 113 | NF | 18-21 | 2.4-2.9 | 0.7-0.9 | 157C | 40-45 | 0.4-0.5 | 3.2-3.6 | 0.8-1.0 | 5.5-6.0 | 1.6-1.8 | 146A | 6 |
| A-48-24 | NF | 20-23 | 2.6 | 0.6-0.8 | 71A/N81A | 77-96 | 0.5-0.6 | 2.4-2.9 | 0.8-10. | 5.5-6.5 | 2.0-3.0 | 146A | 4 |
| X 95 | NF | 23-25 | 3.4-3.7 | 0.9 | N78A/83 | 65-79 | 0.5-0.6 | 3.1-3.5 | 1.0-1.1 | 5.9-6.4 | 2.5 | 147A | 4 |

TABLE 3-continued

Comparison of Certain Plant Characteristics between Normal- and Altered-Flowering *Osteospermum* Genotypes

| | | Ray florets | | | Disc florets | | Foliage - Immature | | Foliage - Mature | | | No. |
|---|---|---|---|---|---|---|---|---|---|---|---|---|
| Code | Type | No. | Length (cm) | Width (cm) | Colour (RHS) | No. | Length (cm) | Length (cm) | Width (cm) | Length (cm) | Width (cm) | Colour (RHS) | basal shoots |
| A-69-1 | NF | 21-25 | 2.7 | 0.8 | 72A/N78A | 93-107 | 0.6 | 2.8 | 0.7-1.1 | 6.3-6.6 | 2.5 | 147A | 4 |
| V 34 | NF | 19-20 | 2.6-2.8 | 0.8-0.9 | 70B/N82A | 72-81 | 0.4-0.5 | 2.5-2.7 | 0.6 | 6.1-6.4 | 2.6 | N137B | 5 |
| W 42 | NF | 16-20 | 2.4-2.6 | 0.7 | 78B/78C/80C | 58-75 | 0.5-0.6 | 2.8 | 0.9-1.0 | 4.3-4.6 | 1.6-1.8 | 146A | 5 |
| A-46-1 | NF | 19-20 | | | N74C + 155D/N82B | 63-70 | 0.5 | 2.3-2.8 | 0.7-0.8 | 5.8-6.3 | 2.5-2.7 | 147A | 4 |

Figure 7:
FIG. 7 shows a whole plant and flowers of OE 2008 248.
Figure 8:
FIG. 8 shows a whole plant and flowers of OE 2008 258.
Figure 9:
FIG. 9 shows a whole plant and flowers of OE 2008 274.
Figure 10:
FIG. 10 shows a whole plant and flowers of OE 2008 285.
Figure 11:
FIG. 11 shows a whole plant and flowers of OE 2008 384.
Figure 12:
FIG. 12 shows a whole plant and flowers of OE 2008 390.

By the described breeding method, which is an aspect of the present invention, 6 genotypes were developed which stably exhibit the new altered phenotype. FIG. 7 through FIG. 12 show pictures of these plants. Table 3 summarizes the comparison of certain plant characteristics in these altered-flowering genotypes compared to normal-flowering *Osteospermum* varieties. As shown in Table 3, unexpectedly, the altered-flowering group consistently differs from the normal-flowering ones in the length of the disc florets, whereas all further plant characteristics show the same variation in the altered-flowering genotypes as in the normal-flowering ones.

From the progenies described previously, 10 altered-flowering *Osteospermum* genotypes were selected and evaluated under different environmental conditions in North and South Europe, East Africa, and the United States covering a broad temperature range and different light regimes. The plants were grown in the greenhouse as well as in the field. The altered-flowering trait was stable under all growing conditions, whereas the expression level as well as the expression of the different phenotypes described above varied depending on the growing conditions. These observations indicate that the mutant allele of the present invention is genetically stable. Additional minor genes may also be involved which determine the number and shape of the additional petals and show gene-environment interaction. The evaluation of further segregating progenies combined with the application of Molecular Marker technology will clarify the inheritance of the new altered flower phenotype in *Osteospermum* in more detail.

EXAMPLES

The following examples are provided to further illustrate the present invention. These examples are not to be construed as limiting the scope of the invention in any manner beyond the limitations set forth in the appended claims. Many variations and modifications may be made while remaining within the spirit and the scope of the invention.

Example 1

Genotype OE 2008 248

Through the breeding process described above, *Osteospermum* genotype OE 2008 248 was developed. OE 2008 248 displays the altered-flower phenotype of the present invention having enlarged disc florets.

TABLE 4

PHENOTYPIC DESCRIPTION OF GENOTYPE OE 2008 248

PLANT:
    Ploidy level: 4x
    Number of basal shoots: 6
    Internode length: 0.05 cm to 1.0 cm
FOLIAGE:
    Immature leaves:
        Length: 3.5 cm
        Width: 0.9 cm
    Mature leaves:
        Length: 4.8 cm to 5.0 cm
        Width: 1.6 cm to 1.9 cm
        Colour: RHS 146A
RAY FLORETS:
    Number: 14 to 16
    Length: 3.0 cm
    Width: 0.7 cm
    Colour of upper surface: RHS 92D
    Colour of lower surface: RHS 85A
DISC FLORETS:
    Number: 80 to 85
    Length: 1.3 cm to 2.1 cm
    Colour of inner surface: RHS 85D
    Colour of outer surface: RHS 91A Example 2

Genotype OE 2008 258

Through the breeding process described above, *Osteospermum* genotype OE 2008 258 was developed. OE 2008 258 displays the altered-flower phenotype of the present invention having enlarged disc florets.

TABLE 5

PHENOTYPIC DESCRIPTION OF GENOTYPE OE 2008 258

PLANT:
    Ploidy level: 4x
    Number of basal shoots: 5
    Internode length: 0.5 cm to 1.0 cm
FOLIAGE:
    Immature leaves:
        Length: 3.2 cm
        Width: 0.8 cm
    Mature leaves:
        Length: 5.2 cm
        Width: 1.9 cm to 2.0 cm
        Colour: RHS 144A
RAY FLORETS:
    Number: 17 to 18
    Length: 2.6 cm to 2.7 cm
    Width: 0.7 cm to 0.8 cm TABLE 5-continued

PHENOTYPIC DESCRIPTION OF GENOTYPE OE 2008 258

Colour of upper surface: RHS 92D
    Colour of lower surface: RHS 76A
DISC FLORETS:
    Number: 73 to 89
    Length: 1.0 cm to 1.9 cm
    Colour of inner surface: RHS 85D
    Colour of outer surface: RHS 76C Example 3

Genotype OE 2008 274

Through the breeding process described above, *Osteospermum* genotype OE 2008 274 was developed. OE 2008 274 displays the altered-flower phenotype of the present invention having enlarged disc florets.

TABLE 6

PHENOTYPIC DESCRIPTION OF GENOTYPE OE 2008 274

PLANT:
    Ploidy level: 4x
    Number of basal shoots: 5
    Internode length: 0.5 cm to 1.0 cm
FOLIAGE:
    Immature leaves:
        Length: 3.2 cm
        Width: 0.8 cm to 0.9 cm
    Mature leaves:
        Length: 4.5 cm to 4.9 cm
        Width: 2.0 cm
        Colour: RHS 146A
RAY FLORETS:
    Number: 25
    Length: 2.6 cm to 2.9 cm
    Width: 0.7 cm to 0.9 cm
    Colour of upper surface: RHS 78B
    Colour of lower surface: RHS 82A
DISC FLORETS:
    Number: 95 to 96
    Length: 1.3 cm to 1.7 cm
    Colour of inner surface: RHS 78A
    Colour of outer surface: RHS 82D Example 4

Genotype OE 2008 285

Through the breeding process described above, *Osteospermum* genotype OE 2008 285 was developed. OE 2008 285 displays the altered-flower phenotype of the present invention having enlarged disc florets.

TABLE 7

PHENOTYPIC DESCRIPTION OF GENOTYPE OE 2008 285

PLANT:
    Ploidy level: 4x
    Number of basal shoots: 5
    Internode length: 0.5 cm to 1.0 cm
FOLIAGE:
    Immature leaves:
        Length: 4.0 cm to 4.5 cm
        Width: 1.2 cm to 1.6 cm
    Mature leaves:
        Length: 7.0 cm to 7.5 cm
        Width: 2.5 cm to 3.5 cm
        Colour: RHS 137A TABLE 7-continued

PHENOTYPIC DESCRIPTION OF GENOTYPE OE 2008 285

RAY FLORETS:
    Number: 22 to 25
    Length: 2.6 cm to 3.0 cm
    Width: 0.6 cm to 0.8 cm
    Colour of upper surface: RHS N74B
    Colour of lower surface: RHS 84A
DISC FLORETS:
    Number: 78 to 85
    Length: 0.8 cm to 2.2 cm
    Colour of inner surface: RHS 72A
    Colour of outer surface: RHS 84A Example 5

Genotype OE 2008 384

Through the breeding process described above, *Osteospermum* genotype OE 2008 384 was developed. OE 2008 384 displays the altered-flower phenotype of the present invention having enlarged disc florets.

TABLE 8

PHENOTYPIC DESCRIPTION OF GENOTYPE OE 2008 384

PLANT:
    Ploidy level: 4x
    Number of basal shoots: 4
    Internode length: 0.5 cm to 1.0 cm
FOLIAGE:
    Immature leaves:
        Length: 3.4 cm
        Width: 1.1 cm
    Mature leaves:
        Length: 4.1 cm
        Width: 2.1 cm
        Colour of upper surface: RHS 146A
RAY FLORETS:
    Number: 23 to 27
    Length: 2.1 cm
    Width: 0.6 cm to 0.7 cm
    Colour of upper surface: RHS 72A
    Colour of lower surface: RHS N80D
DISC FLORETS:
    Number: 94 to 108
    Length: 1.4 cm to 1.7 cm
    Colour of inner surface: RHS 72A
    Colour of outer surface: RHS 84B Example 6

Genotype OE 2008 390

Through the breeding process described above, *Osteospermum* genotype OE 2008 390 was developed. OE 2008 390 displays the altered-flower phenotype of the present invention having enlarged disc florets.

TABLE 9

PHENOTYPIC DESCRIPTION OF GENOTYPE OE 2008 390

PLANT:
    Ploidy level: 4x
    Number of basal shoots: 5
    Internode length: 0.5 cm to 1.0 cm TABLE 9-continued

PHENOTYPIC DESCRIPTION OF GENOTYPE OE 2008 390

FOLIAGE:
    Immature leaves:
        Length: 3.3 cm
        Width: 0.9 cm to 1.1 cm
    Mature leaves:
        Length: 6.5 cm
        Width: 2.0 cm to 2.5 cm
        Colour of upper surface: RHS 146A
RAY FLORETS:
    Number: 19 to 22
    Length: 2.6 cm
    Width: 0.8 cm to 0.9 cm
    Colour of upper surface: RHS 77c and RHS 75D
    Colour of lower surface: RHS 85A
DISC FLORETS:
    Number: 68 to 100
    Length: 1.4 cm to 1.8 cm
    Colour of inner surface: RHS 77C
    Colour of outer surface: RHS 85A Example 7

Incorporating the Mutant Allele KLEDF into *Osteospermum* Varieties

The altered-flowering cultivars having the mutant allele named KLEDF of the present invention maintain functional female and male organs. Therefore, the altered-flowering trait can be incorporated into *Osteospermum* cultivars through conventional breeding, although the execution/implementation of these crosses requires specific skills of the respective pollinators. By crossbreeding, the mutant allele KLEDF of the present invention can be incorporated into a broad range of *Osteospermum* plants having different flower colours and shapes (e.g., spider types) as well as into different foliage types. Furthermore, the mutant allele can be incorporated into plants having different growing habits, e.g., prostrate or hanging types can be developed besides erect or semi-erect types.

Using conventional breeding methods, an *Osteospermum* plant having the mutant allele KLEDF of the present invention is crossed with an *Osteospermum* plant lacking the mutant allele of the present invention. The resulting seeds are sown and the seedlings are grown according to conventional methods. The flowering $F_1$ progenies are then scored for altered-flowering plants. Selected $F_1$ plants are further crossbred or they can be crossed back to their altered-flowering or to their normal-flowering parent in order to combine the altered-flowering phenotype with further desirable plant characteristics. However, depending on the genetic distance between the parents, inbreeding-depression might occur in this backcross progeny. Alternatively, selected plants from this $F_1$ progeny can be outcrossed to selected plants from a different $F_1$ progeny or to another cultivar, which is far related to the respective $F_1$ progeny.

Example 8

Incorporating the Mutant Allele KLEDF into *Osteospermum* Varieties to Create Interspecific Hybrids The mutant allele KLEDF of the present invention can be introduced into an interspecific hybrid made between one species of *Osteospermum* having the mutant allele of the present invention and a different *Osteospermum* species. A selected *Osteospermum* plant having the mutant allele KLEDF is crossed, using conventional methods, as either a male or a female parent, to a selected genotype of any further *Osteospermum* species. Depending on the *Osteospermum* species from which the crossing parent is selected, seeds will set easily, e.g., in crossings with *O. jucundum*. For crosses with plants from less closely related species, specific techniques like bud pollination, removal of the stigma and pollination of the remaining style, $GA_3$-treatments of the pollinated stigmas, and/or embryo rescue of the immature embryo may be necessary. The seeds resulting from the cross are sown and the seedlings are grown according to conventional methods. The flowering $F_1$ progenies are then scored for altered-flowering plants. Further breeding procedure is similar to the procedure described in Example 7.

Example 9

Incorporating the Mutant Allele KLEDF into *Dimorphoteca* Varieties to Create Intergeneric Hybrids Furthermore, the mutant allele KLEDF of the present invention can also be introduced into an intergeneric hybrid through crosses between a selected *Osteospermum* plant having the mutant allele KLEDF of the present invention and a *Dimorphoteca* plant lacking the mutant allele of the present invention. The methods to be used to realize these hybrids correspond to the methods which have been described for interspecific crosses, meaning that specific techniques like bud pollination, removal of the stigma and pollination of the remaining style, $GA_3$-treatments of the pollinated stigmas, and/or embryo rescue of the immature embryo may be necessary to realize these hybrid seedlings.

Example 10

Creating Plants of the Present Invention with the Assistance of Molecular Markers The incorporation of the mutant allele KLEDF of the present invention into a different genetic background requires repeated crossbreeding or backcrossing, meaning that the gene of interest has to be followed over several generations in the respective progenies. In the case of a dominant gene and/or a phenotype, which can easily be selected, selection of the gene of interest can be performed by the phenotype. However, in the case of recessive inheritance and/or a complex phenotype, molecular markers are a very powerful tool to make the selection more efficient and to accelerate the breeding process. Debener (Debener, T., Molecular markers as a tool for analysis of genetic relatedness and selection in ornamentals, *Breeding for Ornamentals: Classical and Molecular Approaches*, 329-345, Kluwer Academic Publishers (2002)) described several examples of successful marker-assisted breeding in ornamentals. Since the techniques of molecular breeding have developed very quickly within the past years, marker-assisted breeding has become even more efficient.

The application of these techniques will enable molecular mapping of the described *Osteospermum* KLEDF mutant allele of the present invention. This information can be used for marker-assisted selection of the mutant allele in segregating progenies.

Example 11

Creating Plants of the Present Invention Using Protoplast Fusion

In some plant species protoplast fusion is a powerful technique to combine the genes of two different species instead of performing crosses between plants of the respective species (Horita, M., Morohashi, H., and Komai, F., Production of fertile somatic hybrid plants between oriental hybrid lily and *Lilium×formolongi, Planta,* 597-601 (2003). Griesbach, R. J., Recent advances in the protoplast biology of flower crops, *Scientia Horticulturae,* 37, 247-256 (1988). Kumar, A. and Cocking, E. C., Protoplast Fusion: A Novel Approach to Organelle Genetics in Higher Plants, *American Journal of Botany,* 741, 1289-1303 (1987)). Besides the addition of two complete genomes, parts of both genomes can be combined. Prerequisite is an efficient protocol for the regeneration of plants from single protoplasts. Even the transmission of just single chromosomes of one partner into the genome of the second partner or the incorporation of the genome of one partner into the cytoplasm of the second partner, as well as a patch-work cytoplasm can be achieved through protoplast fusion. See, for example, Lössl A., Adler, N., Horn, R., Frei, U., and Wenzel, G., Chondriome-type characterization of potato: Mtα, β, γ, δ, ε and novel plastid mitochondrial configurations in somatic hybrids, *Theoretical and Applied Genetics,* 99: 1-10 (1999).

Neither protoplast fusion nor protoplast regeneration has been described for *Osteospermum* or for *Dimorphoteca*. However, since plants of both genera are routinely propagated in tissue culture and can easily be regenerated from leaf explants, protoplast regeneration, as well as protoplast fusion is possible. (See Allavena, A., Giovannini, A., Berio, T., Spena, A., Zottini, M., Accotto, G. P., and Vaira, A. M., Genetic engineering of *Osteospermum* ssp.: a case story, *Acta Hort.,* 508, 129-133 (2000); Giovannini, A., Zottini, M., Morreale, G., Spena, A., and Allavena, A., Ornamental traits modification by rol genes in *Osteospermum ecklonis* transformed with *Agrobacterium tumefaciens,* In Vitro Cell. Dev. Biol. Plant, 35, 70-75 (1999)). Fusion of protoplasts from an *Osteospermum* plant having the mutant allele KLEDF of the present invention with protoplasts from either an *Osteospermum* or a *Dimorphoteca* plant lacking the mutant allele of the present invention, regeneration of plants thereof, and selection of altered-flower individuals among these regenerated fusion products, enables the transmission of the mutant allele of the present invention into new genetic backgrounds.

Example 12

Using Mutagens on Plants of the Present Invention to Create Altered Plants

*Osteospermum* and *Dimorphoteca* plants having the mutant allele KLEDF of the present invention can be used to induce further mutations, leading to further altered flower shapes or new flower colors, altered growing habits, foliage characteristics, etc. Mutants may appear spontaneously or mutations can be induced with Gamma irradiation or through treatment with certain chemical agents like ethyl methanesulfonate (EMS) (Broertjes, C. and van Harten, A. M., Applied mutation breeding for vegetatively propagated crops, Developments in Crop Science 12, Elsevier Science Publishers B. V. (1988); Harten van, A. M., Mutation Breeding: Theory and Practical Applications, Cambridge University Press (1998)). Whereas these treatments mainly induce point mutations or chromosome mutations, genome mutations such as doubling of chromosome numbers can be produced, e.g., by treatment with colchicine. Even tissue culture can induce mutations, which are generally described as somaclonal variation (Chen, W. H., Chen, T. M., Fu, Y. M., and Hsieh, R. M., Studies on somaclonal variation in *Phalaenopsis, Plant Cell Rep,* 18, 7-13 (1998)).

Example 13

Using Transformation on the Plants of the Present Invention

Within the past decades genetic transformation has been a very powerful technique to transfer single genes from one plant into another regardless of crossing barriers. Besides genes for single structural proteins, which might modify flower color or induce specific biotic resistances, genes encoding transcription factors, which manipulate a broader range of complex plant characters, have been successfully transferred even between different plant families or organisms.

A protocol for genetic transformation of *Osteospermum* has been developed and several genes, including the marker gene β-glucuronidase as well as the rolB-gene, have been introduced into this plant species by *Agrobacterium tumefaciens*-mediated gene transfer. The following protocol has been developed, briefly: Leaf segments from *Osteospermum* tissue culture plants are incubated with a disarmed *Agrobacterium tumefaciens* strain which carries a vector with the gene of interest and a gene encoding a specific selectable marker, e.g., nptII for Kanamycin selection. By regeneration under selection pressure according to the selectable marker, transgenic plants can be regenerated from single transformed cells. (See, Allavena, A., Giovannini, A., Berio, T., Spena, A., Zottini, M., Accotto, G. P., and Vaira, A. M., Genetic engineering of *Osteospermum* ssp.: a case story, *Acta Hort.,* 508, 129-133 (2000); Giovannini, A., Zottini, M., Morreale, G., Spena, A., and Allavena, A., Ornamental traits modification by rol genes in *Osteospermum ecklonis* transformed with *Agrobacterium tumefaciens, In Vitro Cell. Dev. Biol. Plant,* 35, 70-75 (1999).) The application of alternative transformation techniques like particle bombardment has not been described yet for *Osteospermum* or *Dimorphoteca*, but may be possible.

The use of genetic transformation is imaginable for both directions: foreign genes can be transferred into an *Osteospermum* or a *Dimorphoteca* plant having the mutant allele KLEDF of the present invention and lead to a plant with completely new characteristics. Alternatively, the mutant allele of the present invention or its respective cDNA can be transferred into foreign genetic backgrounds and induce altered flowers in the resulting transgenic plants.

Example 14

Making Use of the Altered Flower Phenotype for the Production of Hybrid Seed

Most commercially available *Osteospermum* varieties or assortments are vegetatively propagated by cuttings. However, several varieties or assortments of the genera *Osteospermum* and *Dimorphoteca* are propagated by seeds. For hybrid seed production the flowers of the female crossing parent are emasculated and pollinated with pollen of the male parent. To avoid the labour intensive and costly emasculation and hand pollination procedures, a system that inhibits self pollination on the bisexual *Osteospermum* and *Dimorphoteca* plants would be highly desirable. In some plant species biological systems like male sterility or self incompatibility can be used in this respect, but these systems are not described for *Osteospermum* or *Dimorphoteca*. However, in case of the *Osteospermum* and *Dimorphoteca* plants, which exhibit the altered flower phenotype of the present invention, anthers are covered by the enlarged disc florets and hence the pollen is not freely available for pollinating insects. Therefore, hybrid seed production on these plants can be performed without emasculation by insects, which reduces the costs for hybrid seed production significantly.

Example 15

Incorporating the Mutant Allele KLEDF into *Dimorphoteca* Varieties

Through intergeneric hybridization the mutant allele named KLEDF of the present invention can be introduced into the genus *Dimorphoteca*. Furthermore, the altered-flowering trait can be incorporated into a broad range of *Dimorphoteca* cultivars through conventional breeding. By crossbreeding, the mutant allele KLEDF of the present invention can be incorporated into *Dimorphoteca* cultivars having different flower colours and shapes as well as different foliage types. Furthermore, the mutant allele can be incorporated into plants having different growing habits, e.g., prostrate or hanging types can be developed besides erect or semi-erect types.

Using conventional breeding methods, a *Dimorphoteca* plant having the mutant allele KLEDF of the present invention is crossed with a *Dimorphoteca* plant lacking the mutant allele of the present invention. The resulting seeds are sown and the seedlings are grown according to conventional methods. The flowering $F_1$ progenies are then scored for altered-flowering plants. Selected $F_1$ plants are further crossbred or they can be crossed back to their altered-flowering or to their normal-flowering parent in order to combine the altered-flowering phenotype with further desirable plant characteristics. However, depending on the genetic distance between the parents, inbreeding-depression might occur in this backcross progeny. Alternatively, selected plants from this $F_1$ progeny can be outcrossed to selected plants from a different $F_1$ progeny or to another cultivar, which is far related to the respective $F_1$ progeny.

Example 16

Incorporating the Mutant Allele KLEDF into *Dimorphoteca* Varieties to Create Interspecific Hybrids The mutant allele KLEDF of the present invention can be introduced into an interspecific hybrid made between one species of *Dimorphoteca* having the mutant allele of the present invention and a different *Dimorphoteca* species. A selected *Dimorphoteca* plant having the mutant allele KLEDF is crossed, using conventional methods, as either a male or a female parent, to a selected genotype of any further *Dimorphoteca* species. For crosses with plants from less closely related species, specific techniques like bud pollination, removal of the stigma and pollination of the remaining style, $GA_3$-treatments of the pollinated stigmas, and/or embryo rescue of the immature embryo may be necessary. The seeds resulting from the cross are sown and the seedlings are grown according to conventional methods. The flowering $F_1$ progenies are then scored for altered-flowering plants. Further breeding procedure is similar to the procedure described in Example 15. However, since the genus *Dimorphoteca* is representing species with different ploidy levels ranging from 2× to 6×, the resulting hybrids might for example be triploid and not produce viable seeds. Therefore, for further breeding the chromosome number of these plants must e.g. be doubled through treatment with colchicine.

Example 17

Incorporating the Mutant Allele KLEDF into *Osteospermum* Varieties to Create Intergeneric Hybrids Furthermore, the mutant allele KLEDF of the present invention can also be introduced into an intergeneric hybrid through crosses between a selected *Dimorphoteca* plant having the mutant allele KLEDF of the present invention and an *Osteospermum* plant lacking the mutant allele of the present invention. The methods to be used to realize these hybrids correspond to the methods which have been described for interspecific crosses, meaning that specific techniques like bud pollination, removal of the stigma and pollination of the remaining style, $GA_3$-treatments of the pollinated stigmas, and/or embryo rescue of the immature embryo as well as chromosome doubling with colchicine may be necessary to realize these hybrid seedlings.

DEPOSIT INFORMATION

*Osteospermum* seeds containing the KLEDF mutant allele of this invention and capable of displaying the altered-flower phenotype of the present invention have been placed on deposit under the Budapest Treaty with National Collections of Industrial, Food and Marine Bacteria (NCIMB), 23 St Machar Drive, Aberdeen, Scotland, AB24 3RY, United Kingdom under NCIMB Accession No. 41698. The date of deposit was Feb. 26, 2010. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the seeds containing the KLEDF mutant allele will be irrevocably removed by affording access to a deposit of at least 2,500 seeds of the said seeds containing the KLEDF mutant allele with the National Collections of Industrial, Food and Marine Bacteria (NCIMB), 23 St Machar Drive, Aberdeen, Scotland, AB24 3RY, United Kingdom. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. An *Osteospermum* plant comprising at least one dominant mutant allele that produces an altered flower characteristic, wherein said *Osteospermum* plant having an altered flower has at least one inflorescence which has at least one disc floret with an average length of at least 1.3 cm, and wherein a sample of representative seed of the *Osteospermum* plant comprising said dominant mutant allele that produces said altered flower is deposited under NCIMB Accession No. 41698.

2. The *Osteospermum* plant of claim 1, wherein said disc floret ranges from being tubular shaped to a secondary ligulate floret.

3. The *Osteospermum* plant of claim 1, wherein said at least one disc floret has an average length between 1.21 between 1.3 cm and 2.4 cm.

4. The *Osteospermum* plant of claim 1, wherein said at least one disc floret has an average length between 2.41 cm and 4.53 cm.

5. The *Osteospermum* plant of claim 1, wherein said at least one disc floret has an average length between 4.54 cm and 6.0 cm.

6. A method for producing an *Osteospermum* plant having an altered flower, wherein the method comprises crossing the plant of claim 1 with a different *Osteospermum* plant not having an altered flower, and selecting for $F_1$ offspring having an altered flower.

7. An *Osteospermum* seed comprising at least one dominant mutant allele that produces an altered flower characteristic designated KLEDF, wherein a representative sample of *Osteospermum* seed containing said dominant mutant allele that produces an altered flower characteristic was deposited under NCIMB Accession No. 41698.

8. An *Osteospermum* plant, or a part thereof, produced by growing the seed of claim 7.

9. A tissue culture of regenerable cells produced from the plant of claim 1, wherein said cells of the tissue culture are produced from a plant part selected from the group consisting of leaf, pollen, embryo, cotyledon, hypcotyl, meristematic cell, protoplast, root, root tip, pistil, anther, stem, petiole, ray floret, and disc floret.

10. A plant regenerated from said tissue culture of claim 9, wherein said plant has an altered flower having at least one inflorescence that has at least one disc floret with an average length of at least 1.3 cm.

11. A method for producing *Osteospermum* seed containing mutant allele KLEDF, wherein the method comprises crossing the plant of claim 8 with a different *Osteospermum* plant and harvesting the resulting seed.

12. A method for producing an *Osteospermum* plant having an altered flower conferred by mutant allele KLEDF, wherein the method comprises:
    a. obtaining the *Osteospermum* plant of claim 8;
    b. transferring the KLEDF mutant allele from said *Osteospermum* plant to an *Osteospermum* plant not having an altered flower, wherein said transfer is performed via a transgenic method; and
    c. selecting for recipient *Osteospermum* plants containing the KLEDF mutant allele.

13. The method of claim 12, wherein said transgenic transfer of the KLEDF mutant allele is performed into a protoplast or cell culture.

14. A plant produced by the method of claim 12, wherein said plant has the KLEDF allele.

15. A cell or protoplast produced from the plant of claim 14.

16. The cell or protoplast of claim 15, wherein said cell or protoplast is transgenic.

17. A plant produced from the seed of claim 11, wherein said plant has an altered flower conferred by mutant allele KLEDF.

18. A method for transferring mutant allele KLEDF to a different genetic background, wherein the method comprises:
    a. obtaining the the plant of claim 17;
    b. backcrossing said plant to a recipient parent plant not having an altered flower to produce backcross progeny plants;
    c. selecting for backcross progeny plants that contain mutant allele KLEDF;
    d. backcrossing said backcross progeny plants to said recipient parent;
    e. repeating steps (c) and (d) two or more times in succession to produce selected third or higher backcross progeny plants that contain mutant allele KLEDF; and
    f. harvesting the resulting seed.

19. A plant produced from the seed of claim 18.

20. An *Osteospermum* seed containing mutant allele KLEDF produced by the method of claim 11.

21. A method for transferring an altered flower trait to a different genetic background, wherein the method comprises:
    a. obtaining the plant of claim 1;
    b. backcrossing said plant to a recipient parent plant not having an altered flower to produce backcross progeny plants;
    c. selecting for backcross progeny plants to said recipient parent;
    d. repeating steps (c) and (d) two or more times in succession to produce selected third or higher backcross progeny plants that have an altered flower; and
    e. harvesting the resulting seed.

22. A plant grown from the seed produced by the method of claim 21, wherein said plant comprises the dominant mutant allele and has an altered flower.

23. The *Osteospermum* plant of claim 1 having at least one inflorescence that has a disc floret length that is 73% or greater of the length of the ray floret.

24. The *Osteospermum* plant of claim 1 having at least one inflorescence that has a disc floret length that is 67% or greater of the length of the ray floret.

25. The *Osteospermum* plant of claim 1 having at least one inflorescence that has a disc floret length that is 50% or greater of the length of the ray floret.

26. The *Osteospermum* plant of claim 1 having at least one inflorescence that has a disc floret length that is 44% or greater of the length of the ray floret.

27. The *Osteospermum* plant of claim 1 having at least one inflorescence that has a disc floret length that is 38.5% or greater of the length of the ray floret.

28. The *Osteospermum* plant of claim 1 having at least one inflorescence that has a disc floret length that ranges from 38.5% to 43% of the length of the ray floret.

29. The *Osteospermum* plant of claim 1 having at least one inflorescence that has a disc floret length that ranges from 43% to 50% of the length of the ray floret.

30. The *Osteospermum* plant of claim 1 having at least one inflorescence that has a disc floret length that ranges from 50% to 67% of the length of the ray floret.

31. The *Osteospermum* plant of claim 1 having at least one inflorescence that has a disc floret length that ranges from 67% to 73% of the length of the ray floret.

32. The *Osteospermum* plant of claim 1 having at least one inflorescence that has a disc floret length that ranges from 73% to 80% of the length of the ray floret.

* * * * *